US009464263B2

(12) United States Patent
Aussant et al.

(10) Patent No.: US 9,464,263 B2
(45) Date of Patent: Oct. 11, 2016

(54) CORE SHELL MICROCAPSULES AND LIQUID CONSUMER PRODUCT

(75) Inventors: Emmanuel Julien Aussant, Paris (FR); Stuart Bernard Fraser, Little Neston (GB); Jonathan Frank Warr, Paris (FR)

(73) Assignee: Takasago International Corporation, Tokyo (JP)

( * ) Notice: Subject to any disclaimer, the term of this patent is extended or adjusted under 35 U.S.C. 154(b) by 884 days.

(21) Appl. No.: 13/704,317

(22) PCT Filed: Jun. 15, 2011

(86) PCT No.: PCT/JP2011/064197
§ 371 (c)(1),
(2), (4) Date: Mar. 8, 2013

(87) PCT Pub. No.: WO2011/158962
PCT Pub. Date: Dec. 22, 2011

(65) Prior Publication Data
US 2013/0164355 A1   Jun. 27, 2013

(30) Foreign Application Priority Data

Jun. 15, 2010   (EP) .................................... 10305637

(51) Int. Cl.
| C11D 17/00 | (2006.01) |
| C11D 3/50 | (2006.01) |
| A61K 8/11 | (2006.01) |
| C11D 3/00 | (2006.01) |

(52) U.S. Cl.
CPC ................ C11D 3/505 (2013.01); A61K 8/11 (2013.01); C11D 3/0015 (2013.01); C11D 17/0013 (2013.01); C11D 17/0039 (2013.01); A61K 2800/412 (2013.01)

(58) Field of Classification Search
CPC .............. A61K 8/11; A61K 2800/412; C11D 3/0013; C11D 3/505
See application file for complete search history.

(56) References Cited

U.S. PATENT DOCUMENTS

| 6,716,526 | B2* | 4/2004 | Weston ..................... B01J 13/14 427/162 |
| 6,869,923 | B1* | 3/2005 | Cunningham ............ A61K 8/11 510/101 |
| 2005/0112152 | A1 | 5/2005 | Popplewell et al. |
| 2006/0058437 | A1 | 3/2006 | Martin et al. |
| 2006/0248665 | A1 | 11/2006 | Pluyter et al. |
| 2007/0138672 | A1* | 6/2007 | Lee ........................... B01J 13/14 264/4.1 |
| 2008/0194454 | A1 | 8/2008 | Morgan et al. |
| 2009/0035365 | A1 | 2/2009 | Popplewell et al. |
| 2010/0168275 | A1 | 7/2010 | Zhao et al. |
| 2010/0286018 | A1 | 11/2010 | Hentze et al. |

FOREIGN PATENT DOCUMENTS

| CN | 101678307 A | 3/2010 |
| EP | 1 502 646 A1 | 2/2005 |
| EP | 1 964 542 A1 | 9/2008 |
| EP | 2 204 156 A1 | 7/2010 |
| WO | 97/47288 A1 | 12/1997 |
| WO | 00/59616 A1 | 10/2000 |
| WO | 02/074430 A1 | 9/2002 |
| WO | 2009/090169 A1 | 7/2009 |
| WO | 2009/100553 A1 | 8/2009 |
| WO | 2009/153695 A1 | 12/2009 |
| WO | 2010/053940 A1 | 5/2010 |
| WO | 2010/070602 A2 | 6/2010 |

OTHER PUBLICATIONS

Office Action, dated Jan. 6, 2014, issued by the State Intellectual Property Office of the People's Republic of China in counterpart Chinese Application No. 201180029901.8.
Office Action, Issued by the State Intellectual Property Office of P.R. China, Dated Aug. 14, 2014, In counterpart Chinese Application No. 201180029901.8.
Communication dated Jul. 27, 2015 issued by the State Intellectual Property Office of P.R. China in counterpart Chinese Patent Application No. 201180029901.8.
Communication issued on Mar. 31, 2015 by the Japanese Patent Office in related Application No. 2012-549195.
Communication issued on Jan. 21, 2015 by The State Intellectual Property Office of P.R. China in related application No. 201180029901.8.
International Search Report (PCT/ISA/210), dated Jul. 30, 2012, issued by the International Searching Authority in corresponding International Application No. PCT/JP2011/064197.
Written Opinion (PCT/ISA/237), dated Jul. 30, 2012, issued by the International Searching Authority in corresponding International Application No. PCT/JP2011/064197.
European Search Report dated Dec. 6, 2010 issued by the European Patent Office in counterpart European Patent Application No. 10 30 5637.

\* cited by examiner

Primary Examiner — Ali Soroush
(74) Attorney, Agent, or Firm — Sughrue Mion, PLLC

(57) ABSTRACT

The present invention relates to core shell microcapsules for use in liquid consumer products, wherein: the microcapsule shell is made of starting materials such that 50%-100% by weight of said materials have a density equal to or less than 1.05 $g/cm^3$; the microcapsule core contains a fragrance composition comprising 20-100% by weight of at least one cyclic fragrance material with a density greater than 0.950 $g/cm^3$ and a ClogP in the range of from 1.00 to 6.00; the weight ratio of core materials to shell materials is in the range from about 50:1 to about 1:1.

15 Claims, No Drawings

CORE SHELL MICROCAPSULES AND LIQUID CONSUMER PRODUCT

TECHNICAL FIELD

The invention relates to core shell type microcapsules of which fragrance compositions are incorporated into the core to control the delivery and release of fragrance and optionally other benefit agents, when used as components within liquid household, laundry, personal care and cosmetic products. More specifically the invention relates to microcapsules in which the wall composition is formed from predominantly low density starting materials.

The invention further relates to the use of these microcapsules in liquid consumer products, especially household cleaners, laundry products, and personal care, and cosmetic products, especially thickened and shear thinning liquids.

BACKGROUND ART

It is known to encapsulate water insoluble perfumes or other non-fragrance materials, in small capsules often termed microcapsules, typically having diameters between 1 and 1000 micrometers (microns μm), for a variety of reasons relating to the protection, delivery and release of the perfume or other beneficial materials from consumer products.

Microcapsules are described in Kirk Othmer's Encyclopaedia of Chemical Technology 5th edition. One type of microcapsules, referred to as a wall or shell or core shell microcapsule, comprises a generally spherical shell of water and oil insoluble materials, typically a network polymer material, within which perfume or other hydrophobic material is contained.

Microcapsules can be prepared by many chemical reaction types and differing reagents. Many of the reactions used to prepare polymers can be adapted to prepare microcapsule walls. Amongst the most common chemical reactions used to prepare microcapsules having particle sizes greater than 1 μm are: condensation reactions such as those involving aldehydes such as formaldehyde or glutaraldehyde and amine or phenolic compounds such as melamine, urea or resorcinol. Microcapsules of this type are currently used in household products.

Co-acervation is another encapsulation technique which is widely used to form microcapsules in which pre formed polymers react together such that the product is insoluble in both aqueous and oil phases and forms a protective shell at the interface of an oil and water emulsion. Interfacial polymerization is a further option and involves the reaction of oil soluble compounds with water soluble compounds to form a network of polymers which are insoluble in both oil and water. Examples of such reactions are oil soluble acid chlorides such as diterephthaloyl chloride reacting with water soluble amines to form shell walls. Free radical polymerization of unsaturated compounds such as vinylic, acrylic, or styrenic compounds is another way of producing microcapsules and is becoming increasingly important as manufacturers either try to avoid compounds regarded as unsafe in some way, or to solve the problems encountered with other microcapsule types. To those skilled in the art it is recognized that it is possible to combine these various microcapsule wall forming processes so as to either form sequential layers of microcapsule walls or a single wall using combinations of reactions or post capsule formation to add additional materials to modify the properties of the wall.

Current microcapsules are not entirely satisfactory. The manufacturing process may leave residual amounts of chemicals such as formaldehyde in the product which is undesirable. It is also known that microcapsule contents may leak during storage in the product. For these and other reasons manufacturers still seek improved methods of microcapsule production. The current invention addresses another specific problem of microcapsules in liquid products, that of maintaining a homogeneous microcapsule dispersion in a liquid product. Depending on the size of the microcapsules, viscosity of the liquid phase and density difference between the liquid phase and microcapsules this problem may be more or less serious. Microcapsules containing fragrance oils, made by any process in which the starting materials used to prepare the microcapsule wall are predominantly of low density or result in a thin walled capsule may separate on storage due to density differences and it can be difficult to keep such microcapsules uniformly dispersed in aqueous or higher density, liquid products.

When such microcapsules are incorporated in liquid consumer products e.g. personal care products such as shampoos, hair conditioners, body washes, shower gels, laundry products such as fabric conditioners or liquid laundry detergents or household cleaners such as kitchen surface cleaners, problems can arise, with the microcapsules either creaming (rising to the surface) or settling over time, especially while the product is stored. The creaming or settling is due to differences in density between the microcapsule and the surrounding liquid. Many aqueous based consumer products liquid household cleaners, liquid laundry products and personal care and cosmetic products have densities around 1.00 gram per cubic centimeter ($g/cm^3$), while many organic compounds have densities much lower than 1.00 $g/cm^3$. So a microcapsule containing a high proportion of fragrance oils or other hydrophobic oils may have a lower density than the liquid phase of the product in which the microcapsules are dispersed, hence these microcapsules will tend to rise or cream over time. If the microcapsule wall material is thin, or made from lower density starting materials this creaming phenomenon will be more noticeable.

Since it may not be desirable or even possible to prepare microcapsules of different (usually smaller) size to reduce creaming as this may have other consequences, such as affecting the ease of breaking the walls for those microcapsules which rely on friability for content release. Moreover less material is encapsulated into a smaller microcapsule requiring a higher proportion of wall material relative to content and a larger number of microcapsules to contain the same volume of core material which consequently may affect product attributes such as colour and also the manufacturing cost. It may also be undesirable to increase the viscosity of the liquid product in which the microcapsules are dispersed, hence it is advantageous if the densities of the microcapsules and liquid phase can be more equally balanced.

Patent Literature 1 relates to core shell microcapsules in which high density cyclic fragrance materials are encapsulated. The shell of the microcapsules mainly comprises an aminoplast resin.

Patent Literature 2 describes adding solvents to core shell encapsulated fragrances but stipulates that the fragrances must have ClogP greater than 3.3, preferably greater than 8.

Patent Literature 3 describes density modifiers for co-acervate microcapsules for detergent liquid products but only describes materials which lower the density of the microcapsule.

Patent Literature 4 also describes modifying the microcapsule contents in order to balance the density with the surrounding liquid.

Patent Literature 5 describes balancing the densities of poly alpha olefin particles with surface coatings of wax and relatively high density inorganic or mineral particulates.

Patent Literature 6 describes modifying the density of fragrance containing microcapsules using high density materials in the core. Particularly exemplified are inorganic materials such as titanium dioxide although other high density materials such as brominated vegetable oil are also mentioned.

CITATION LIST

Patent Literature

PTL 1: EP 2204156 A1
PTL 2: US 2005/112152 A1
PTL 3: EP-A-1502646
PTL 4: WO 00/59616
PTL 5: US 2006/0058437 A1
PTL 6: US 2009/0035365 A1

SUMMARY OF INVENTION

Technical Problem

With regard to US 2005/112152, it is clear from the context that density was not a consideration in selecting these materials since the majority of those named have densities lower than 1.0 g/cm$^3$ and the higher ClogP requirements suggest that larger alkyl groups are preferred such as glyceryl tributyrate rather than glyceryl triacetate although the latter would be preferred as a density increasing ingredient.

With regard to WO 00/59616, the materials suggested for raising the density are not very suitable for personal care, laundry and household products being some high density salts, or high density hydrophobic liquids such as those containing halogens. It is not desirable, or in many cases permissible to include halogenated organic compounds into microcapsules intended for domestic consumer products since many such compounds are believed to have adverse effects on the environment and/or on health.

With regard to US 2009/0035365 A1, while acknowledging that the microcapsule wall material contributes to the overall density this document does not recognize how much harder it is to balance the density of a microcapsule with the surrounding liquid if the microcapsule wall is made from low density starting materials such as styrenes or acrylates compared with those made from higher density starting materials such as melamine or urea and formaldehyde. Nor does this application teach that the microcapsule core can be modified by using a combination of high density fragrance ingredients and other high density organic compounds.

Surprisingly few organic compounds have densities greater than 0.950 g/cm$^3$ even fewer have densities greater than 1.00 g/cm$^3$. It is also noticeable that compounds having higher densities tend to comprise a substantial proportion of oxygen, nitrogen and sulphur atoms in their molecular formulae and/or possess rings such as aromatic rings in their chemical structures. However such compounds are often quite hydrophilic owing to the polar nature of many functional groups containing oxygen, nitrogen or sulphur atoms. Consequently it is surprising that such hydrophilic compounds can be efficiently encapsulated by emulsion polymerization techniques.

A further requirement is that encapsulated molecules should not leak from the microcapsules during storage and it has been suggested that more water soluble molecules leak quite quickly, especially from microcapsules made by amine and aldehyde condensation reactions (see EP-A-1533364).

So while it is advantageous if the densities of microcapsules can be closely balanced to the density of the liquid product into which they are to be dispersed, this is increasingly difficult to achieve for liquid products as the density increases beyond 0.900 g/cm$^3$, especially if the microcapsule walls are constructed from low density materials. Furthermore from the diverse constraints on the microcapsule wall such as: ease of manufacture, robustness to handling, stability in the product and release of microcapsule content at the appropriate time in use; and constraints on the core material: that the fragrance must be of sufficient quality and intensity to be acceptable in a premium commercial product, that it should be stable during microcapsule manufacture and not leak on storage, it is surprising that an additional density constraint can be imposed on the perfumer and yet they are able to provide consumer desirable fragrances.

Solution to Problem

It is an object of the present invention to provide a core shell microcapsule, in particular for use in liquid household or personal products having a density in the range from 0.900 g/cm$^3$ to 1.400 g/cm$^3$, wherein the microcapsule shell (or wall) is made of starting materials such that 50%-100% by weight of said materials have a density equal to or less than 1.05 g/cm$^3$;

the microcapsule core contains a fragrance composition, which composition comprises:

a) 20-100% by weight of at least one cyclic fragrance ingredient (category A material) with a density greater than 0.950 g/cm$^3$ and a ClogP in the range from 1.00 to 6.00;

b) 0-50% by weight of at least one oil soluble organic compound (category B material) having a density greater than 0.950 g/cm$^3$;

c) 0-80% by weight of at least one category C material; where the sum of a), b) and c) equals 100%, wherein the weight ratio of core materials to shell materials is in the range from about 50:1 to about 1:1.

At least 50% by weight of the shell of the microcapsules is made of (starting) materials having a density equal to or less than 1.05 g/cm$^3$. It is advantageous if at least 60% by weight, preferably at least 70% by weight, more preferably at least 80% by weight and especially preferably at least 90% by weight of the materials have a density equal to or less than 1.05 g/cm$^3$. In a preferred aspect, the density of the above-mentioned materials is in the range from 0.700 g/cm$^3$ to 1.05 g/cm$^3$, preferably from 0.800 g/cm$^3$ to 1.05 g/cm$^3$, more preferably in the range of from 0.850 g/cm$^3$ to 1.05 g/cm$^3$.

The fragrance composition which is encapsulated in the microcapsule of the invention comprises from 20 to 100% by weight of at least one cyclic fragrance material with a density greater than 0.950 g/cm$^3$ and a ClogP in the range from 1.00 to 6.00. It is advantageous if the fragrance composition comprises from 25% to 100% by weight, preferably from 30% to 100% by weight, more preferably from 40% to 100% by weight, even more preferably from 50% to 100% by weight and especially preferably from 70% to 100% by weight of at least one cyclic fragrance material with a density greater than 0.950 g/cm$^3$ and a ClogP in the range from 1.00 to 6.00. In one embodiment, the said at least one cyclic fragrance material has a density greater than 0.950 g/cm$^3$ and up to 2.000 g/cm$^3$, preferably in the range from 1.000 g/cm$^3$ to 1.500 g/cm$^3$ and more preferably from 1.050 g/cm³ to 1.400 g/cm³. In another embodiment, which can be combined with the previous embodiment, the said at least one cyclic fragrance material has a ClogP value in the range from 1.00 to 5.00, preferably from 2.00 to 5.00, and more preferably from 2.00 to 4.50.

The core shell microcapsule of the invention is suitable for use in liquid consumer products which have a density in the range from 0.900 g/cm³ to 1.400 g/cm³, preferably from 0.900 g/cm³ to 1.250 g/cm³; such liquid consumer products typically have a viscosity in the range from 100 to 5,000 mPas. In a preferred aspect of the invention the liquid consumer product is a predominantly aqueous product.

That is, the present invention provides the following core shell microcapsule and liquid consumer product.

(1) A core shell microcapsule, comprising a core and a shell wherein:

the shell of the microcapsule is formaldehyde-free and is made of starting materials such that 50%-100% by weight of said materials have a density equal to or less than 1.05 g/cm³; and the core of the microcapsule contains a fragrance composition, the fragrance composition comprising:

a) 20-100% by weight of at least one cyclic fragrance material with a density greater than 0.950 g/cm³ and a ClogP in the range from 1.00 to 6.00;

b) 0-50% by weight of at least one oil soluble organic compound having a density greater than 0.950 g/cm³; and c) 0-80% by weight of at least one category C material;

where the sum of a), b) and c) equals 100%, wherein the weight ratio of core materials to shell materials is in the range from about 50:1 to about 1:1.

(2) The core shell microcapsule according to (1), wherein at least 60% by weight of the starting materials have a density equal to or less than 1.05 g/cm³.

(3) The core shell microcapsule according to (2), wherein at least 70% by weight of the starting materials have a density equal to or less than 1.05 g/cm³.

(4) The core shell microcapsule according to any one of (1) to (3), wherein the said starting materials have a density in the range from 0.700 g/cm³ to 1.05 g/cm³.

(5) The core shell microcapsule according to (4), wherein the said starting materials have a density in the range from 0.800 g/cm³ to 1.05 g/cm³.

(6) The core shell microcapsule according to (4), wherein the said starting materials have a density in the range from 0.850 g/cm³ to 1.05 g/cm³.

(7) The core shell microcapsule according to any one of (1) to (6), wherein the said starting materials comprise at least about 50% by weight of (meth)acrylic acid and/or (meth)acrylates.

(8) The core shell microcapsule according to (7), wherein the said starting materials comprise at least about 60% by weight of (meth)acrylic acid and/or (meth)acrylates.

(9) The core shell microcapsule according to any one of (1) to (6), wherein the said starting materials comprise from 20% to 75% by weight of one or more cross-linking polymers.

(10) The core shell microcapsule according to any one of (1) to (9), wherein the fragrance composition comprises from 25% to 100% by weight of at least one cyclic fragrance material with a density greater than 0.950 g/cm³ and a ClogP in the range from 1.00 to 6.00.

(11) The core shell microcapsule according to (10), wherein the fragrance composition comprises from 30% to 100% by weight of at least one cyclic fragrance material with a density greater than 0.950 g/cm³ and a ClogP in the range from 1.00 to 6.00.

(12) The core shell microcapsule according to (10), wherein the fragrance composition comprises from 40% to 100% by weight of at least one cyclic fragrance material with a density greater than 0.950 g/cm³ and a ClogP in the range from 1.00 to 6.00.

(13) The core shell microcapsule according to (10), wherein the fragrance composition comprises from 50% to 100% by weight of at least one cyclic fragrance material with a density greater than 0.950 g/cm³ and a ClogP in the range from 1.00 to 6.00.

(14) The core shell microcapsule according to any one of (1) to (13), wherein the said at least one cyclic fragrance material has a density in the range from 1.000 g/cm³ to 1.500 g/cm³.

(15) The core shell microcapsule according to (14), wherein the said at least one cyclic fragrance material has a density in the range from 1.050 g/cm³ to 1.400 g/cm³.

(16) The core shell microcapsule according to any one of (1) to (15), wherein the said at least one cyclic fragrance material has a ClogP in the range from 1.00 to 5.00.

(17) The core shell microcapsule according to (16), wherein the said at least one cyclic fragrance material has a ClogP in the range from 2.00 to 5.00.

(18) The core shell microcapsule according to (16), wherein the said at least one cyclic fragrance material has a ClogP in the range from 2.00 to 4.50.

(19) The core shell microcapsule according to any one of (1) to (18), wherein the weight ratio of core materials to shell materials is in the range from about 20:1 to about 1:1.

(20) The core shell microcapsule according to (19), wherein the weight ratio of core materials to shell materials is in the range from about 10:1 to about 1:1.

(21) The core shell microcapsule according to any one of (1) to (20), wherein the core composition has a density in the range from 0.950 g/cm³ to 1.100 g/cm³.

(22) The core shell microcapsule according to (21), wherein the core composition has a density in the range from 0.975 g/cm³ to 1.050 g/cm³.

(23) A liquid consumer product having a density in the range from 0.900 g/cm³ to 1.400 g/cm³, which comprises the core shell microcapsule as defined in any one of (1) to (22).

(24) The liquid consumer product according to (23), which has a density in the range from 0.900 g/cm³ to 1.250 g/cm³.

(25) The liquid consumer product according to (23) or (24), which is a household, laundry, personal care or cosmetic composition.

(26) The liquid consumer product according to (25), which is a fabric softener.

(27) The liquid consumer product according to (26), which comprises more than 50% by weight water and from about 3% to about 40% by weight of cationic surfactant(s).

Advantageous Effects of Invention

The invention can provide core shell type microcapsules of which fragrance compositions are incorporated into the core to control the delivery and release of fragrance and optionally other benefit agents, when used as components within liquid household, laundry, personal care and cosmetic products.

DESCRIPTION OF EMBODIMENTS

In this specification, all percentages quoted are weight percent unless otherwise stated. Percentages which refer to fragrance compositions are based on the composition prior to emulsification and encapsulation and not to the encapsulated fragrance composition.

In this text 'predominantly' means greater than 50% by weight.

A starting material is a material added in the mixture to create the microcapsule wall or shell which undergoes a chemical reaction involving the formation of covalent bonds such that the reaction cannot be reversed in a few minutes at ambient temperature by a simple physical process such as dilution with water or changing the pH.

In this text, '(meth)acrylic acid' is intended to mean acrylic acid and methacrylic acid. Likewise '(meth)acrylate' is intended to mean acrylate and methacrylate.

All documents cited in this specification are incorporated herein by reference.

The density of any substance is defined as the quotient of its mass and volume and is expressed in grams per cubic centimeter ($g/cm^3$). Several methods are available for determining the density of substances; the most common ones are described in the OECD Guideline For The Testing of Chemicals No 109 adopted by the Council on Jul. 27, 1995. ASTM D4052 describes the procedure to measure densities of a liquid using a digital density meter using the oscillating U-tube principle.

Thus densities of liquid ingredients can be measured at 20° C. or 25° C. following the procedure of ASTM D4052, using e.g. a Mettler Toledo DR40 digital density meter or a pycnometer. Densities for materials with melting points above 35° C. can be measured by other methods as is well known to those of ordinary skill in the art.

Density is a ratio of two measured values and so subject to bias and variation depending on the methods and test conditions used. Reproducibility with a digital density meter is less than 0.001 $g/cm^3$ and bias also less than 0.001 $g/cm^3$ compared with a pycnometer method. Thus for the purposes of the present specification, densities are only quoted to three decimal places and the fourth decimal place is rounded up or down according to the usual convention. In case of disputed values for liquid samples at ambient temperature, the digital density meter is the designated method for density determination as described in ASTM D4052.

In the present specification, the term "high density" when used for core materials is used for densities greater than 0.950 $g/cm^3$ and up to 2.000 $g/cm^3$. Low density when used in the context of microcapsule wall starting materials means materials having densities in the range from 0.700 $g/cm^3$ to 1.05 $g/cm^3$.

Viscosities are measured at 25° C. using a Brookfield LVT viscometer with spindle No. 3 at 30 rpm.

For the purpose of the present specification, the term organic compound means a chemical compound containing only atoms from among, but not necessarily containing all of, the following: carbon, hydrogen, oxygen, sulphur, nitrogen and chlorine. A high density organic compound is a compound consisting of atoms from among the group carbon, hydrogen, oxygen, sulphur, nitrogen and chlorine, having a density greater than 0.950 $g/cm^3$ preferably greater than 1.000 $g/cm^3$ and even more preferably greater than 1.050 $g/cm^3$.

The term cyclic or the word ring in the context of molecular structure in the present specification refers to a series of atoms which form a closed ring within a molecule e.g. cyclohexane rather than the open chain aliphatic compound hexane. Aromatic rings are those capable of undergoing electrophilic substitution reactions rather than the addition reactions which occur with non aromatic unsaturated compounds. They can also be defined as planar rings having (4n+2) Π electrons according to Hückels rule and include arenes and heteroarenes. The term cyclic also includes heterocyclic rings and substituted ring molecules. Further definitions of chemical nomenclature as used in this text can be found in "G. P. Moss, P.A.S. Smith and D. Tavernier, Pure and Applied Chemistry, vol. 67 pp 1307-1375 1995."

Fragrance Containing Composition

An essential part of the invention is that the microcapsule core contains a fragrance composition and that at least 20% of that fragrance composition should be high density, cyclic, fragrance ingredients. In the context of this specification, the term fragrance composition is understood to be synonymous with the terms "perfume composition" or "perfume" and to refer to a mixture of olfactively active materials providing a pleasant smell. The term fragrance ingredient which is also synonymous with the terms "fragrance component", "perfume ingredient" and "perfume component" is taken to mean any individual material which may be an ingredient within the fragrance composition even though that perfume ingredient may itself comprise many individual chemical compounds and possess a pleasant smell. This distinction is understood by those familiar with the art of fragrance creation.

A wide variety of odiferous materials are known for perfumery use, including materials such as alkenes, alcohols, aldehydes, ketones, esters, ethers, nitriles, amines, oximes, acetals, amides ketals, thiols, thioketones, imines, etc. Without wishing to be limited, the fragrance ingredients of the core composition will preferably have molecular weights of less than 325 atomic mass units, preferably less than 300 atomic mass units and more preferably less than 275 atomic mass units to ensure sufficient volatility to be noticeable when the microcapsules release. Furthermore the fragrance ingredients will preferably have molecular weights greater than 100 atomic mass units, preferably greater than 125 atomic mass units as lower masses may be too volatile to be effective as part of a fragrance, or too water soluble to be emulsified during encapsulation. It is preferred if ingredients of the fragrance compositions do not contain strongly ionizing functional groups such as sulphonates, sulphates, or quaternary ammonium ions; it is also preferred if the ingredients of fragrance compositions do not contain any halogen atoms. Thus fragrance ingredients used in the invention will preferably be comprised of compounds containing only atoms from among, but not necessarily all of, the following: hydrogen, carbon, oxygen, nitrogen and sulphur.

Fragrance ingredients are described more fully in S. Arctander, Perfume Flavors and Chemicals. Vols. I and II, Montclair, N.J. and in Allured's Flavor and Fragrance Materials 2007 ISBN 978-1-93263326-9 published by Allured Publishing Corp.

Preferably fragrance ingredients which are suitable for inclusion in the core of a core shell microcapsule are unaffected by the chemical reactions of the encapsulation process.

Naturally occurring plant oils and exudates comprising complex mixtures of various chemical components are also known for use as perfumes, and such materials can be used herein although each material is considered as a single ingredient despite it being well known that most natural extracts are mixtures of compounds. The principal chemical components of most natural oils are known, and thus for the most part they can be assessed in the same way as synthetic aroma chemicals.

In order that the encapsulated fragrance should give a noticeable fragrance on release and be appreciated as a high quality fragrance appropriate for a premium consumer product, a fragrance composition for encapsulation should contain at least 4 fragrance ingredients, preferably at least 6 fragrance ingredients, more preferably at least 8 fragrance ingredients, and even more preferably at least 10 fragrance ingredients, which can comprise a mixture of natural and synthetic ingredients chosen to create any desired odour. From a practical viewpoint, the fragrance composition should not comprise more than 50 fragrance ingredients. Additionally no single fragrance ingredient should comprise more than 70% by weight of the total fragrance composition, preferably no single fragrance ingredient should comprise more than 60% by weight of the total fragrance composition, and more preferably no fragrance ingredient should comprise more than 50% by weight of the total fragrance composition.

ClogP refers to the octanol/water partitioning coefficient (P) of fragrance ingredients. The octanol/water partitioning coefficient of a perfume ingredient is the ratio between its equilibrium concentrations in octanol and in water. The partitioning coefficients of perfume ingredients are more conveniently given in the form of their logarithm to the base 10, log P. Thus the perfume ingredients of category A in this invention have ClogP of about 1.00 to 6.00, preferably in the range 2.00 to 5.00 and more preferably in the range 2.00 to 4.50. The log P values of many perfume ingredients have been reported; for example, the Pomona92 database, available from Daylight Chemical Information Systems, Inc. (Daylight CIS), Irvine, Calif., contains many, along with citations to the original literature. The "calculated log P" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental log P values in the selection of perfume ingredients which are useful in the present invention. There are several alternative methods of calculating or estimating log P values which can show some variation in values. Even calculations within a given set of software may change over time as the algorithms are modified to give results which are closer to measured values. To remove any uncertainty the ClogP values reported herein are most conveniently calculated by the "CLOGP" program available within the Chemoffice Ultra Software version 9 available from CambridgeSoft Corporation, 100 CambridgePark Drive, Cambridge, Mass. 02140 USA or CambridgeSoft Corporation, 8 Signet Court, Swanns Road, Cambridge CB5 8LA UK. The ClogP values are preferably used instead of the experimental log P values in the selection of perfume ingredients which are useful in the present invention. For natural oils or extracts, the composition of such oils can be determined by analysis or using the compositions published in the ESO 2000 database published by BACIS (Boelens Aroma Chemical Information Service, Groen van Prinsterlaan 21, 1272 GB Huizen, The Netherlands).

The fragrance composition for encapsulation comprises fragrance materials belonging to either category A or C as defined below. In short, fragrance ingredients within category A materials have the following characteristics: they contain a ring within the normal representation of the molecular formula and they have densities greater than 0.950 g/cm$^3$ at 20° C. or such higher temperature that the density can properly be measured. They also conform to the above definition of fragrance materials in that they have ClogP values in the range from 1.00 to 6.00 and molecular weights in the range from 100 amu to 325 amu. Fragrance ingredients within category C need not contain a ring, but cyclic fragrance materials should have densities equal to or less than 0.950 g/cm$^3$ at 20° C. or such higher temperature that the density can properly be measured, while non cyclic fragrance compounds may have higher or lower densities than 0.950 g/cm$^3$.

High Density Cyclic Fragrance Ingredients (Category A)

An essential feature of the invention is that 20% to 100% by weight of the fragrance composition should be comprised of at least 1, preferably at least 3, more preferably at least 6 and especially preferably at least 10 cyclic fragrance ingredients, each ingredient having a density greater than 0.950 g/cm$^3$. Suitable cyclic fragrance ingredients include those having densities greater than 0.950 g/cm$^3$ and up to 2.000 g/cm$^3$, preferably in the range from 1.000 g/cm$^3$ to 1.500 g/cm$^3$ and more preferably from 1.050 g/cm$^3$ to 1.400 g/cm$^3$, with ClogP values in the range from 1.00 to 6.00, preferably from 1.00 to 5.00, more preferably from 2.00 to 5.00 and even more preferably from 2.00 to 4.50. Such high density cyclic fragrance ingredients must also comply with the requirements of perfume ingredients stated previously. Table 1 below lists examples of a number of common high density perfume materials which have densities greater than 0.950 g/cm$^3$. The list is intended to exemplify high density cyclic perfume materials and not to be comprehensive, nor in any way limiting on the invention. The density of the materials was measured at 20° C. following the procedure described in ASTM D4052 unless otherwise stated.

TABLE 1

| Compound | CAS Number | Density (g/cm$^3$) | ClogP |
|---|---|---|---|
| ALLYL PHENOXY ACETATE | 007493-74-5 | 1.100 | 2.45 |
| AMYL SALICYLATE | 2050-08-0 | 1.065$^c$ | 4.45 |
| ISOAMYL SALICYLATE | 87-20-7 | 1.053$^c$ | 4.45 |
| ANISYL PROPIONATE | 007549-33-9 | 1.07$^d$ | 2.41 |
| BENZOPHENONE | 119-61-9 | 1.067$^c$ | 3.18 |
| BENZYL ACETATE | 140-11-4 | 1.055 | 1.96 |
| BENZYL BENZOATE | 000120-51-4 | 1.112 | 3.94 |
| BENZYL SALICYLATE | 000118-58-1 | 1.176 | 4.16 |
| ISO BORNYL ACETATE | 125-12-2 | 0.986$^c$ | 4.04 |
| CEDANOL | 7070-15-7 | 0.986$^c$ | 3.12 |
| CINNAMYL ACETATE | 000103-54-8 | 1.050 | 2.55 |
| CIS 3 HEXENYL SALICYLATE | 65405-77-8 | 1.059 | 4.50 |
| COUMARIN | 91-64-5 | 1.237$^c$ | 1.41 |
| CYCLOHEXYL SALICYLATE | 025485-88-5 | 1.112$^a$ | 4.37 |
| CYCLACET ™ | 005413-60-5 | 1.071 | 2.88 |
| CYCLAPROP ™ | 17511-60-3 | 1.047 | 3.41 |
| DIETHYL PHTHALATE | 84-66-2 | 1.12$^d$ | 2.65 |
| DIMETHYL PHTHALATE | 131-11-3 | 1.19$^d$ | 1.66 |
| DIHYDROEUGENOL | 002785-87-7 | 1.038$^d$ | 2.88 |
| DIHYDROISOJASMONATE | 37172-53-5 | 1.003$^c$ | 3.09 |
| DIMETHYL RESORCINOL | 000151-10-0 | 1.055$^d$ | 2.15 |
| DIMETHYL TEREPHTHALATE | 120-61-6 | 1.200 | 1.66 |
| 3,4-DIMETHOXY TOLUENE | 000494-99-5 | 0.990 | 2.30 |
| DIPHENYL ETHER | 000101-84-8 | 1.075 | 4.24 |
| ETHYL ANISATE | 000094-30-4 | 1.103$^d$ | 2.81 |
| ETHYL BENZOATE | 000093-89-0 | 1.050 | 2.64 |
| 4-ETHYL GUAIACOL | 002785-89-9 | 1.050 | 2.35 |
| ETHYL 3-PHENYL GLYCIDATE | 000121-39-1 | 1.102 | 2.43 |

TABLE 1-continued

| Compound | CAS Number | Density (g/cm³) | ClogP |
|---|---|---|---|
| ETHYL 3-METHYL-3-PHENYL GLYCIDATE | 77-83-8 | 1.094$^c$ | 2.95 |
| ETHYL SALICYLATE | 000118-61-6 | 1.130 | 2.86 |
| ETHYL VANILLIN | 121-32-4 | 1.130 at 80° C. | 1.81 |
| ETHYLENE BRASSYLATE | 105-95-3 | 1.018$^c$ | 3.02 |
| EUGENOL | 000097-53-0 | 1.070 | 2.40 |
| EUGENYL ACETATE | 000093-28-7 | 1.055 | 2.30 |
| HELIOBOUQUET | 001205-17-0 | 1.163 | 2.37 |
| HELIOTROPINE | 120-57-0 | 1.267$^c$ | 1.76 |
| HELIOTROPYL ACETATE | 326-61-4 | 1.24$^c$ | 1.78 |
| INDOLE | 000120-72-9 | 1.086$^b$ | 2.13 |
| ISOBUTYL SALICYLATE | 000087-19-4 | 1.060 | 3.79 |
| ISOEUGENYL PHENYL ACETATE | 000120-24-1 | 1.119$^d$ | 4.33 |
| ISOEUGENOL | 000097-54-1 | 1.099$^c$ | 2.58 |
| MAGNOLIA INDENE | 027606-09-3 | 1.087 | 2.45 |
| 4-METHOXYACETOPHENONE | 000100-06-1 | 1.082 | 1.80 |
| METHYL BENZOATE | 000093-58-3 | 1.089 | 2.11 |
| METHYL CINNAMATE | 001754-62-7 | 1.057$^c$ | 2.46 |
| METHYL SALICYLATE | 000119-36-8 | 1.180 | 2.33 |
| 2-METHYL-4-PROPYL-1,3-OXATHIANE | 59323-76-1 | 1.050$^c$ | 1.22 |
| PHENYLACETALDEHYDE GLYCERYL ACETAL | 29895-73-6 | 1.157 | 1.08 |
| PHENYL BENZOATE | 000093-99-2 | 1.230 | 3.04 |
| 2-PHENYLETHYL ACETATE | 000103-45-7 | 1.088 | 2.28 |
| PHENYL ETHYL BENZOATE | 000094-47-3 | 1.093$^d$ | 4.22 |
| PHENYL ETHYL PHENYL ACETATE | 000102-20-5 | 1.082$^d$ | 3.92 |
| PHENYL ETHYL SALICYLATE | 000087-22-9 | 1.154$^d$ | 4.43 |
| PHENYL SALICYLATE | 000118-55-8 | 1.260 | 3.84 |
| PHENOXY ETHYL ISO BUTYRATE | 000103-60-6 | 1.044$^d$ | 2.92 |
| VANILLIN | 121-33-5 | 1.056$^c$ | 1.28 |
| VANILLIN ISOBUTYRATE | 20665-85-4 | 1.12$^d$ | 1.72 |
| VELTOL PLUS | 4940-11-8 | 1.379$^c$ | 1.13 |
| WATERMELON KETONE | 28940-11-6 | 1.161 at 40° C. | 1.80 |

$^a$Kao MSDS for cyclohexyl salicylate
$^b$measured at 60° C. reported in JCS Perkin Trans 2 p199-200 (2002)
$^c$Beilstein
$^d$Sigma-Aldrich catalogue and references therein.
Cyclacet is 3a,4,5,6,7,7a-hexahydro-4,7-methano-1H-inden-5(or 6)-yl acetate and a trade mark of International Flavors and Fragrances.
Cyclaprop is 3a,4,5,6,7,7a-hexahydro-4,7-methano-1H-inden-5(or 6)-yl propionate and a trade mark of International Flavors and Fragrances.

A preferred group of high density cyclic fragrance materials for inclusion into microcapsule cores includes: amyl salicylate, benzyl acetate, benzophenone, benzyl salicylate, cis 3-hexenyl salicylate, coumarin, cyclohexyl salicylate, Cyclacet™, Cyclaprop™, diethyl phthalate, dimethyl phthalate, ethylene brassylate, ethylvanillin, eugenol, heliotropine, indole, isobornyl acetate, isoeugenol, methyl anthranilate, methyl benzoate, oxane (2-methyl-4-propyl-1,3-oxathiane), phenoxy ethyl isobutyrate, 2-phenylethanol, 2-phenylethyl acetate, vanillin, vanillin isobutyrate, watermelon ketone.

Essential oils or natural extracts which have a density greater than 0.950 g/cm³ and contain more than 50% by weight of fragrance materials with a ClogP value in the range from 1.00 to 6.00 are considered to be Category A materials in their entirety.

Oil Soluble Organic Compounds (Category B)

An optional but often necessary feature of the invention is the inclusion into the fragrance composition of 0-50% by weight, preferably 10-45% by weight and more preferably 20-40% by weight of one or more oil soluble organic compounds having a density greater than 0.950 g/cm³, typically in the range from 1.050 g/cm³ to 1.750 g/cm³, more preferably from 1.100 g/cm³ to 1.500 g/cm³, and especially preferably from 1.150 g/cm³ to 1.400 g/cm³. Organic has the same meaning as previously defined in the specification. Generally the oil soluble organic compounds of category B are solvents or diluents used in fragrances or ingredients with a sufficiently low odour that they cannot on their own be used to make a commercially acceptable perfume composition. Category B ingredients may also be used in food products. Since these materials are not fragrance ingredients they dilute the fragrance hence they are usually not desirable but may be necessary to achieve the desired final capsule density. Category B materials have high densities so can affect a significant increase in density whilst only comprising a small percentage of core material by weight.

In one embodiment, high density compounds are high density oil soluble organic polyacyl compounds. Oil soluble in the context of the present specification means materials which have a solubility greater than 1.5 g per 100 g of diethyl phthalate at 20° C. after 48 hours. Polyacyl means the compounds possess at least two acyl groups. These acyl groups can be either or both of esters or amide groups. Moreover the high density oil soluble poly acyl compounds must have a molecular weight in the range from 100 amu to 1500 amu, preferably from 125 amu to 1000 amu and more preferably from 150 to 750 amu, contain at least 2 ester or amide groups per molecule, and have densities greater than 0.950 g/cm³ and up to 2.000 g/cm³, preferably in the range from 1.050 g/cm³ to 1.750 g/cm³, more preferably from 1.100 g/cm³ to 1.500 g/cm³, and especially preferably from 1.150 g/cm³ to 1.400 g/cm³.

Suitable high density oil soluble organic polyacyl compounds include compounds with a density greater than 1.000 g/cm³, represented by formulae 1 to 4 below:

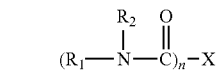

1

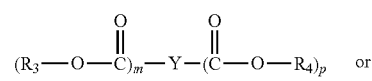

2 or

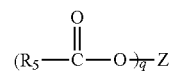

3

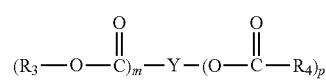

4 in which:
$R_1$ and $R_2$, are independently hydrogen or a methyl group or can be bound to a carbon within X to form a lactam;
$R_3$ and $R_4$ are independently a $C_1$ to $C_6$ linear or branched alkyl group;
$R_5$ is a methyl or an ethyl group;
n, m and q have an integer value from 1 to 12, preferably from 2 to 8 and more preferably from 3 to 8;
p has an integer value from 0 to 12;
X, Y and Z are independently a $C_1$ to $C_{15}$ substituted or unsubstituted linear, branched or cyclic alkyl, alkenyl, alkynyl, alkaryl or aryl group.

Table 2 lists a number of high density oil soluble organic ingredients which are intended to exemplify the range of materials but not to be comprehensive, nor in any way limiting on the invention. The density of the materials was taken from the Sigma-Aldrich catalogue 2008-2009 (or from the online version) and references therein.

TABLE 2

| COMPOUNDS | CAS Number | Density (g/cm$^3$) |
|---|---|---|
| ACETYL TRIETHYL CITRATE | 77-89-4 | 1.136 |
| DIETHYL MALEATE | 141-05-9 | 1.064 |
| DIETHYL MALONATE | 105-53-3 | 1.055 |
| DIETHYL ADIPATE | 141-28-6 | 1.009 |
| DIMETHYL ADIPATE | 627-93-0 | 1.062 |
| DIETHYL SUCCINATE | 123-25-1 | 1.047 |
| DIETHYL TARTARATE | 87-91-2 | 1.204 |
| GLYCERYL TRIACETATE | 106-76-1 | 1.21 |
| SUCROSE OCTA-ACETATE | 126-14-7 | 1.28 |
| SUCROSE DIACETATE HEXAISOBUTYRATE | 27216-37-1 | 1.15 |
| GLYCERYL TRIPROPIONATE | 139-45-7 | 1.08 |
| TRIETHYL CITRATE | 000077-93-0 | 1.137 |

Preferred high density oil soluble poly acyl organic compounds include sucrose octa-acetate, glyceryl triacetate, glyceryl tripriopionate, diethyl tartarate, triethyl citrate and acetyl triethyl citrate or any mixture of these compounds.

Other Fragrance Ingredients and Organic Compounds (Category C)

An optional but often desirable feature of the invention is the inclusion into the fragrance composition of 0-80% by weight, preferably 10-70% by weight, or more preferably 20-60% by weight of one or more category C ingredients. Such category includes:

cyclic fragrance ingredients with densities equal to or less than 0.950 g/cm$^3$. Without wishing to be restrictive in any way, examples of such conventional fragrance ingredients include but are not limited to: ortho and para tertiary butyl cyclohexyl acetate, lilial, bourgeonal, limonene, α and β, pinenes, α damascone, β damascenone, iso cyclocitral, dimethyl benzyl carbinyl acetate, α ionone, β ionone and methyl isodihydrojasmonate;

non cyclic compounds with densities which may be greater or less than 0.950 g/cm$^3$; non-limiting examples of such compounds include dihydromyrcenol, citronellol, citronellyl acetate, linalool, linalyl acetate, cis hex-3-en-1-ol, octanal, decanal, dodecanal and undecylenic aldehyde.

Assignment of Ingredients to Categories

The categories can be considered to have a hierarchy: category A precedes B then C. Compounds are assigned to the highest category whose criteria they meet completely. So compounds which meet the criteria of category A are assigned to that category in preference to any other category. For example, sucrose octaacetate which contains a ring, has too high a molecular weight for category A, but as a high density multi acyl compound fulfills all the criteria of category B. Any organic compounds which do not fit the criteria of either of category A or B are assigned to category C.

Solvents

Olfactively weak or neutral solvents may also be present in a typical fragrance. Solvents are defined as liquid organic compounds which can generally be added at up to 50% by weight to a fragrance composition without significantly affecting the odour of the fragrance. In the perfume industry it is quite common to dissolve solid fragrance materials in a suitable solvent or to dilute powerful materials, used at low levels, with a solvent to facilitate manufacture. Some solvents can be considered density modifying ingredients; some hydrophobic solvents may also aid the emulsification process, and ensure better capture of the fragrance materials within the core of the capsule. In the present specification and appended claims, solvents are conventionally assigned to one of categories A, B or C according to how they match the definitions of those categories. For example:

benzyl benzoate and diethyl phthalate which both contain an aromatic ring, have a molecular weight in the range from 100 amu to 325 amu, and a ClogP value in the range from 1.00 to 6.00, are assigned to category A;

dialkyl adipates and citrate esters, such as acetyl tributyl citrate, are assigned to category B;

isopropyl myristate, propylene glycol, dipropylene glycol, and various carbitol ethers such as the Dowanol™ series from Dow Chemical, are classified in category C.

Core Composition

The microcapsule core may contain, in addition to the fragrance composition described above, other agents well-known to those of ordinary skill in the art. Non-limiting examples of such agents include malodour counteracting agents; essential oils; aromatherapeutic materials; chemaesthetic agents; vitamins; insect repellents, such as ethylbutylacetylaminopropionate or N,N-diethyltoluamide; antioxidants, such as tocopheryl acetate, ascorbyl palmitate, retinoyl palmitate, butylated hydroxytoluene or butylated hydroxyanisole; sunscreen compounds, such as octyl-methoxycinnamate, benzitriazolyldodecyl p-cresol or butyl-methoxydibenzoylmethane; densifying agents, such as those mentioned in US 2009/035365; cooling agents, such as N,2,3-trimethyl-2-isopropylbutamide or menthyl lactate; anti-microbial agents; pro-fragrances molecules which react to release fragrance compounds; emulsifiers; colourants; stabilisers; and thickening agents.

It is advantageous if the core composition as described above has a density in the range from about 0.950 g/cm$^3$ to about 1.100 g/cm$^3$, preferably from about 0.975 g/cm$^3$ to about 1.050 g/cm$^3$.

Microcapsules

The fragrance-containing composition encapsulated in core shell microcapsules of the invention is particularly appropriate for use in liquid products. The term microcapsule as used herein includes the encapsulation of perfume and other materials or actives in small capsules (i.e. microcapsules), typically having an average particle size in the range from 1 micrometer to 500 micrometers, preferably from 2 micrometers to 200 micrometers, more preferably from 5 micrometers to 100 micrometers and especially preferably from 10 micrometers to 50 micrometers. The average particle size can be determined in several different ways, however the preferred technique is by light scattering using a Malvern Mastersizer with the average particle size being taken as the median particle size D(0.5) value.

An important parameter for capsule density is the thickness of the shell. This parameter is also important for friable capsules which release perfume by breaking. If the shell is too thick the capsules will not break in use, however if the shell is too thin the capsules will not survive the manufacturing and shipping involved in making a product. Also the proportion of core material to shell material is an important factor in determining capsule density. In order for capsules to be friable yet strong enough to survive processing, the weight ratio of core materials to shell materials is in the range from about 50:1 to about 1:1, preferably from about 30:1 to about 1:1, more preferably from about 20:1 to about 1:1, even more preferably from about 10:1 to about 1:1.

Core shell microcapsules typically comprise a shell of water-insoluble or at least partially water-insoluble material, typically polymeric material, within which the perfume and other material is contained. Microcapsules are described in the following references: US 2003/215417 A1; US 2003/216488 A1; US 2003/165692 A1; US 2004/071742 A1; US 2004/071746 A1; US 2004/072719 A1; US 2004/072720 A1; EP-A-1393706; US 2003/203829 A1; US 2003/195133 A1; US 2004/087477 A1; US 2004/106536 A1; U.S. Pat. No. 6,200,949; U.S. Pat. No. 4,882,220; U.S. Pat. No. 4,917,920; U.S. Pat. No. 4,514,461; US RE 32,713; U.S. Pat. No. 4,234,627.

Microcapsules may be prepared using a range of conventional methods known to those skilled in the art for making core shell microcapsules, such as interfacial polymerization, free radical polymerization, vinyl polymerization or polycondensation. See e.g., U.S. Pat. No. 3,516,941, U.S. Pat. No. 4,520,142, U.S. Pat. No. 4,528,226, U.S. Pat. No. 4,681,806, U.S. Pat. No. 4,145,184; GB-A-2073132; WO 99/17871; and MICROENCAPSULATION: Methods and Industrial Applications Edited by Benita and Simon (Marcel Dekker, Inc. 1996). It is recognized, however, that many variations with regard to materials and process steps are possible whilst still essentially manufacturing a core shell microcapsule. Non-limiting examples of starting materials suitable for making the shells of microcapsules include (meth)acrylic acid, (meth)acrylates, urethanes, styrene or other vinylic compounds. The starting materials may comprise, in addition to the materials listed above, one or more cross-linking polymers such as divinyl benzene, allyl acrylate, allyl methacrylate, ethylene glycol diacrylate, ethylene glycol dimethacrylate, triethylene glycol dimethacrylate, tetramethyleneglycol dimethacrylate, propylene glycol dimethacrylate, 1,4-butanediol diacrylate, 1,4-butanediol dimethacrylate, 1,6-hexanediol diacrylate, 1,6-hexanediol dimethacrylate, trimethylolpropane trimethacrylate, methallyl methacrylamide, N,N-methylene bisacrylamide, pentaerythritoltriallyl ether, pentaerythritol tetraacrylate, pentaerythritol tetramethacrylate or toluene diisocyanate. It is worth noting that the shell of the microcapsules is formaldehyde-free.

The starting materials preferably have a density in the range from 0.700 g/cm$^3$ to 1.05 g/cm$^3$, more preferably from 0.800 g/cm$^3$ to 1.05 g/cm$^3$, even more preferably from 0.850 g/cm$^3$ to 1.05 g/cm$^3$.

Without wishing to be limited table 3 below illustrates the densities of some starting materials commonly used in the preparation of core shell microcapsule walls. The density of the materials was taken from the Sigma-Aldrich catalogue 2008-2009 (or from the online version) and references therein.

TABLE 3

| Starting Material | Density (g/cm$^3$) |
|---|---|
| Methyl methacrylate | 0.936 |
| Methacrylic acid | 1.015 |
| 2-(diethylamino)ethylmethacrylate | 0.933 |
| 2-hydroxyethyl methacrylate | 1.073 |
| N-butyl methacrylate | 0.894 |
| Ethyl methacrylate | 0.917 |
| Ethylene glycol dimethacrylate | 1.051 |
| Isobutyl methacrylate | 0.886 |
| Isodecyl methacrylate | 0.878 |
| Lauryl methacrylate | 0.868 |
| Tetraethylene glycol dimethacrylate | 1.082 |
| Triethylene glycol dimethacrylate | 1.092 |
| Trimethylolpropane trimethacrylate | 1.06 |
| Hydroxypropyl methacrylate | 1.066 |
| 1,4-butanediol diacrylate | 1.03 |
| 1,4-butanediol dimethacrylate | 1.023 |
| Styrene | 0.909 |
| Divinyl benzene | 0.914 |

TABLE 3-continued

| Starting Material | Density (g/cm$^3$) |
|---|---|
| Vinyl acetate | 0.934 |
| Vinylpyrrolidone | 1.040 |
| 6-caprolactone | 1.030 |
| Ethyl 2-cyanoacrylate | 1.060 |
| Toluene diisocyanate | 1.22 |
| 4,4'-methylene diphenylisocyanate | 1.18 |

The microcapsule shell (or wall) is formed from starting materials such that from 50% to 100% by weight of said materials have a density equal to or less than 1.05 g/cm$^3$. In one aspect at least 60% by weight, preferably at least 70% by weight, more preferably at least 80% by weight, and especially at least 90% by weight of the starting materials have a density equal to or less than 1.05 g/cm$^3$.

In one aspect, the microcapsules are formed by free radical polymerization, notably vinyl polymerization, of unsaturated compounds such as styrene, (meth)acrylic acid and/or (meth)acrylates. (Meth)acrylic acid and/or (meth)acrylates are preferred starting materials; when present they make up at least about 50% by weight, preferably at least about 60% by weight, of the starting materials. Examples of such preferred starting materials include acrylic acid, methacrylic acid, ($C_1$-$C_4$)alkyl methacrylates, hydroxy($C_1$-$C_4$) alkyl methacrylates, mono- or di-($C_1$-$C_4$)alkyl amino($C_1$-$C_4$)alkyl methacrylates and mixtures thereof.

When present, the cross-linking polymers may be contained in the starting materials in an amount of from about 20% to about 75% by weight, preferably from about 30% to about 60% by weight, and more preferably from about 30% to about 50% by weight. Preferred cross-linking polymers include 1,4-butanediol acrylate, 1,4-butanediol dimethacrylate, divinyl benzene, ethyleneglycol dimethacrylate, trimethylolpropane trimethacrylate and tetramethyleneglycol dimethacrylate. In this aspect, the sum of all starting materials equals 100%.

Secondary wall polymers may also be used as appropriate to improve the shell wall, e.g., anhydrides and their derivatives, particularly polymers and co-polymers of maleic anhydride as disclosed in US 2004/087477 A1. For the purposes of this document the shell wall is understood to comprise all materials which become part of the shell wall at the end of the preparation i.e. all water insoluble wall materials. In this aspect of the invention, the sum of all starting materials and secondary wall polymers is 100%.

Those skilled in microcapsule manufacture will appreciate that there are many variations which may be introduced into the manufacture of core shell microcapsules such as varying ingredient proportions and process parameters but which still fall within the general description for core shell preparation as described in the present specification and the cited references. However one variation which may be noted is that of dissolving salts of alkali metals or ammonia and amine derivatives into the aqueous phase prior to the encapsulation reaction to help in the formation of a stable emulsion phase when less hydrophobic ingredients are present in the core composition. These salts may be of inorganic acids such as hydrochloric, sulphuric, phosphoric or nitric acids.

The microcapsules of the present invention, in one embodiment, are friable in nature. Friability refers to the propensity of the microcapsules to rupture or break open when subjected to direct external pressures or shear forces. For purposes of the present invention, the microcapsules utilized are "friable" if, while attached to fabrics treated therewith, they can be ruptured by the forces encountered when the microcapsules-containing fabrics are manipulated by being worn or handled (thereby releasing the contents of the microcapsules).

The microcapsules of the present invention are distinguished from moisture-activated microcapsules, such as those microcapsules comprising of starch or cyclodextrin that burst upon contact with moisture such as those described in U.S. Pat. No. 5,246,603 which are not considered to be core shell microcapsules.

Liquid Household, Laundry, Personal Care and Cosmetic Products

The formulations and ingredients of liquid household, laundry and personal care and cosmetic products in which microcapsules containing fragrance compositions of the invention may be used are well known to those skilled in the art, reference may be made to the following works which are incorporated herein by reference:

Formulating Detergents and Personal Care Products A guide to Product Development by L Ho Tan Tai, ISBN 1-893997-10-3 published by the AOCS Press. Also to Volume 67 of the Surfactant Science Series Liquid Detergents ISBN 0-8247-9391-9 (Marcel Dekker Inc), as well as to the following patents or patent applications:

Fabric softeners and conditioners: U.S. Pat. No. 6,335,315; U.S. Pat. No. 5,674,832; U.S. Pat. No. 5,759,990; U.S. Pat. No. 5,877,145; U.S. Pat. No. 5,574,179.

Liquid Laundry detergents: U.S. Pat. No. 5,929,022; U.S. Pat. No. 5,916,862; U.S. Pat. No. 5,731,278; U.S. Pat. No. 5,470,507; U.S. Pat. No. 5,466,802; U.S. Pat. No. 5,460,752; U.S. Pat. No. 5,458,810.

Shampoos and Hair Conditioners: U.S. Pat. No. 6,162,423; U.S. Pat. No. 5,968,286; U.S. Pat. No. 5,935,561; U.S. Pat. No. 5,932,203; U.S. Pat. No. 5,837,661; U.S. Pat. No. 5,776,443; U.S. Pat. No. 5,756,436; U.S. Pat. No. 5,661,118; U.S. Pat. No. 5,618,523.

Liquid household, laundry and personal care and cosmetic products can have a range of densities typically from 0.800 to 1.600 g/cm$^3$, preferably for liquid compositions containing surfactants, emulsified oils, solvents and inorganic material either in solution or suspended in the formulation, from 0.900 to 1.400 g/cm$^3$, preferably from 0.900 g/cm$^3$ to 1.250 g/cm$^3$ and more preferably from 0.950 g/cm$^3$ to 1.150 g/cm$^3$. Those which are predominantly aqueous compositions will tend to have densities close to 1.000 g/cm$^3$. The term predominantly aqueous liquid product means a product in which water is the largest ingredient by weight percentage. In one aspect, the liquid product is a fabric softener, also known as fabric conditioner. Such products usually contain more than 50% by weight water and from about 3% to about 40% by weight of cationic surfactant(s) and their densities are close to and may be less than 1.000 g/cm$^3$.

Some non-aqueous or low aqueous liquid product formulations contain substantial proportions of polar solvents such as alcohols and glycols consequently their densities may be greater than 1.000 g/cm$^3$. Table 4 below contains some illustrative examples of the densities of some commercial brands of liquid household, laundry, personal care and cosmetic products. The list is illustrative and is neither meant to be comprehensive nor limiting on the invention in any way.

TABLE 4

| Product | Density (g/cm$^3$) | Manufacturer |
|---|---|---|
| European Ariel Concentrated Detergent Liquid | 1.070 | Procter and Gamble |
| European Ariel Standard Detergent Liquid | 1.040 | Procter and Gamble |
| European Aerial Hydroactiv | 1.050 | Procter and Gamble |
| Dash/Bold Concentrated Liquid | 1.100 | Procter and Gamble |
| Dash/Bold Standard Liquid | 1.070 | Procter and Gamble |
| All Small and Mighty | 1.050-1.070 | Unilever |
| Comfort Pearls | 1.042 | Unilever |
| Persil Liquid tablet | 1.026 | Unilever |
| Le Chat Concentre Gel Fr | 1.070-1.080 | Henkel |
| Super Croix Standard Liquid | 1.020-1.030 | Henkel |
| Persil Colour Gel (De) | 1.070-1.080 | Henkel |
| Persil Kraft Gel (De) | 1.070-1.080 | Henkel |
| US Tide 2X Concentrate Fragrance Free Sensitive Skin | 1.081 | Procter and Gamble |
| US Tide Regular Fragrance Free Sensitive Skin | 1.048 | Procter and Gamble |
| US Tide 2X Concentrate HE | 1.040-1.090 | Procter and Gamble |
| US 2X Clean Burst Concentrate | 1.031 | Arm & Hammer |
| US Fresh Scent and Oxy Clean | 1.042 | Arm & Hammer |
| Japanese Attack Bio Gel | 1.027 | Kao |
| Japanese Liquid Top | 1.039 | Lion |
| Japanese Aerial Ion Power | 1.043 | Procter and Gamble |
| Dove Cool Moisture Shampoo | 1.054 | Unilever |
| Dove Douche Soin de Beaute (Fr) | 1.034 | Unilever |
| Palmolive Tahiti Homme Shampoo et Douche (Fr) | 1.018 | Colgate |
| Palmolive hand wash | 1.042 | Colgate |
| Lenor Sensitive Conc | 0.99 | Procter and Gamble |
| Lenor Sensitive Regular | 1.00 | Procter and Gamble |

On incorporating microcapsules into liquid products there is a tendency for the microcapsules to "cream" i.e. rise to the surface, or to settle, to the bottom of the container, on extended storage over a normal temperature range (4° C.-40° C.) due to differences in density between the liquid and the microcapsules. While many factors affect the rate at which the creaming or settling occurs it is helpful if the products themselves slow or prevent separation. From Stokes law it is apparent that there is a relationship between a product's viscosity and the density difference between the densities of the microcapsule and liquid product. The greater the difference in densities the more viscous a product needs to be to suspend the microcapsules. This is easily illustrated by products which are sufficiently viscous that they can suspend air bubbles for quite long periods after shaking. The corollary is that when the microcapsule and product are more closely balanced in density the product need not be so viscous for the microcapsules to remain dispersed. Hence it is preferable if the liquid household, laundry, personal care or cosmetic products into which microcapsules are introduced have viscosities in the range from 20 to 10,000 mPas, preferably from 100 to 5000 mPas, more preferably from 1,000 to 5000 mPas measured at 25° C. using a Brookfield LVT viscometer with spindle No 3 at 30 rpm. For some product formulations the product viscosity may change during prolonged storage or at elevated temperature. Thus the values given above should not only be applied to freshly made samples but also to samples that have been stored for at least 12 weeks at 40° C.

Microcapsule fragrance dosage into liquid products depends on the total payload of benefit agent to be delivered. Various aspects influence the dosage: the microcapsule dispersion concentration, the proportion of fragrance within the microcapsule and the amount of material necessary to create the effect desired. Measured as dry weight of microcapsules after removal of all water and solvents from the microcapsule preparation the dosage of microcapsule into liquid products should be in the range from 0.01 to 10% by weight of the liquid product composition, preferably from 0.05% to 2.5% by weight, more preferably from 0.1 to 1.25% by weight of the composition. The microcapsules may be incorporated into the products by any conventional means usually as a liquid dispersion added at a suitable stage in the process but usually after any high shear mixing stage.

The present invention will be now disclosed in more details by the following illustrative, but not limiting, examples.

EXAMPLES

Example 1

(Reference): Fragrance Composition 1

Table 5 below gives the formulation of fragrance composition 1.

TABLE 5

| Ingredient | CAS No | wt % | Density (g/cm$^3$) | Category |
|---|---|---|---|---|
| Linalool | 78-70-6 | 26.0 | 0.870 | C |
| Isoamyl acetate | 123-92-2 | 24.0 | 0.879 | C |
| Ethylene Brassylate | 105-95-3 | 9.8 | 1.018 | A |
| d-Limonene | 5989-27-5 | 13.0 | 0.844 | C |
| Ethyl 2-methylbutyrate | 7452-79-1 | 12.0 | 0.879 | C |
| Butyl acetate | 123-86-4 | 3.0 | 0.886 | C |
| Tricyclodecenyl propionate | 17511-60-3 | 6.0 | 1.10 | A |
| Decalactone gamma | 706-14-9 | 4.0 | 0.946 | C |
| Cis hex-3-en-1-yl acetate | 3681-71-8 | 2.0 | 0.897 | C |
| Isopropyl myristate | 110-27-0 | 0.2 | 0.850 | C |

Fragrance composition 1 contains 15.8% by weight of category A ingredients and has a density of 0.8939 g/cm$^3$ as measured at 20° C. according to ASTM D4052.

Example 2

Fragrance Composition 2

Table 6 below gives the formulation of fragrance composition 2.

TABLE 6

| Ingredient | CAS No | wt % | Density (g/cm$^3$) | Category |
|---|---|---|---|---|
| Benzyl salicylate | 118-58-1 | 23.0 | 1.17 | A |
| Allyl caproate | 123-68-2 | 17.3 | 0.887 | C |
| Isobornyl acetate | 125-12-2 | 17.2 | 0.986 | A |
| Ethylene brassylate | 105-95-3 | 11.3 | 1.018 | A |
| Beta pinene | 127-91-3 | 5.7 | 0.880 | C |
| d-Limonene | 5989-27-5 | 5.7 | 0.844 | C |
| 2,4,6 trimethyl-4-phenyl-1,3dioxane | 5182-36-5 | 10.0 | 0.977 | A |
| Octanal | 124-13-0 | 5.6 | 0.811 | C |
| Cis hex-3-en-1-yl acetate | 3681-71-8 | 4.0 | 0.897 | C |
| Isopropyl myristate | 110-27-0 | 0.2 | 0.850 | C |

Fragrance composition 2 contains 61.5% by weight of category A ingredients and has a density of 0.9852 g/cm$^3$ as measured at 20° C. according to ASTM D4052.

Example 3

Fragrance Composition 3

Fragrance composition 3 was prepared by adding a high density fragrance ingredient to and removing a low density fragrance ingredient from fragrance composition 1. Table 7 below gives the formulation of fragrance composition 3.

TABLE 7

| Ingredient | CAS No | wt | Density (g/cm$^3$) | Category |
|---|---|---|---|---|
| Benzyl salicylate | 118-58-1 | 23.20 | 1.17 | A |
| Linalool | 78-70-6 | 19.97 | 0.870 | C |
| Iso amyl acetate | 123-92-2 | 18.43 | 0.879 | C |
| Ethylene Brassylate | 105-95-3 | 7.68 | 1.018 | A |
| d-Limonene | 5989-27-5 | 9.98 | 0.844 | C |
| Ethyl 2-methylbutyrate | 7452-79-1 | 9.22 | 0.879 | C |
| Butyl acetate | 123-86-4 | 2.30 | 0.886 | C |
| Tricyclodecenyl propionate | 17511-60-3 | 4.61 | 1.10 | A |
| Decalactone gamma | 706-14-9 | 3.07 | 0.946 | C |
| Cis hex-3-en-1-yl acetate | 3681-71-8 | 1.54 | 0.897 | C |

Fragrance composition 3 contains 35.49% by weight of category A ingredients and has a density of 0.967 g/cm$^3$ as measured at 20° C. according to ASTM D4052.

In the following examples 4 to 7, all the materials used for the preparation of the microcapsules were purchased from Sigma-Aldrich unless otherwise mentioned.

Example 4

Preparation of Microcapsules

A 250 ml closed stirred vessel was fitted with an anchor type stirrer. It was charged in succession with phase A and then Phase B:

| Phase A | |
|---|---|
| Water | 105.86 g |
| Sodium dodecyl sulphate | 0.255 g |
| Phase B | |
| Fragrance composition 4* | 42.6 g |
| Methacrylic acid | 13.1 g |

-continued

| | |
|---|---|
| Methyl methacrylate | 4.6 g |
| 1,4-butane diol diacrylate | 11.3 g |
| Lauroyl peroxide | 0.300 g |
| Phase C | |
| Potassium peroxo disulphate @ 2.5% | 0.49 g |
| Water | 9.61 g |

*fragrance MUPCHE022E available from Takasago, having a density of 0.906 g/cm$^3$ (as measured at 20° C. according to ASTM D4052) and containing about 24% by weight of category A ingredients Phase B and then phase A were added to the reactor and the agitator started at time T0. The charge was processed to a finely dispersed emulsion by adjusting the stirring speed to 1100 rpm for 50 minutes at 35° C. while a stream of nitrogen gas was bubbled through the reaction mixture to remove oxygen. The temperature was raised to 70° C. over the course of 15 minutes and allowed to react for a further 4 hours. If required small portions (10 g) of degassed water were added, during the course of the reaction, if the sample became too viscous. After 3 hours 0.4 g of phase C was added to the mixture. After 4 hours the reaction was stopped whereby a microcapsule dispersion was obtained. The weight ratio of core material to shell material in this example is 1.47:1; those skilled in the art can understand how the ratio can be altered by modifying the quantities of ingredients.

Example 5

Preparation of Microcapsules

A 250 ml closed stirred vessel was fitted with an anchor type stirrer. It was charged in succession with phase A and then Phase B:

| | |
|---|---|
| Phase A | |
| Water | 105.86 g |
| Sodium dodecyl sulphate | 0.255 g |
| Phase B | |
| Fragrance composition 5* | 42.55 g |
| Methacrylic acid | 6.52 g |
| Methyl methacrylate | 2.30 g |
| 1,4-butane diol diacrylate | 5.65 g |
| Lauroyl peroxide | 0.300 g |
| Phase C | |
| Potassium peroxo disulphate @ 2.5% | 0.49 g |
| Water | 9.61 g |

*fragrance MUGRPF056D available from Takasago, having a density of 0.974 g/cm$^3$ (as measured at 20° C. according to ASTM D4052) and containing about 55% by weight of category A ingredients Phase B and then phase A were added to the reactor and the agitator started at time T0. The charge was processed to a finely dispersed emulsion by adjusting the stirring speed to 1100 rpm for 50 minutes at 35° C. while a stream of nitrogen gas was bubbled through the reaction mixture to remove oxygen. The temperature was raised to 70° C. over the course of 15 minutes and allowed to react for a further 4 hours. After 3 hours 0.4 g of phase C was added to the mixture. After 4 hours the reaction was stopped whereby a microcapsule dispersion was obtained.

The weight ratio of core material to shell material in this example is 2.94:1; those skilled in the art can understand how the ratio can be altered by modifying the quantities of ingredients.

Example 6

Preparation of Microcapsules

A 250 ml closed stirred vessel was fitted with an anchor type stirrer. It was charged in succession with phase A and then Phase B.

| | |
|---|---|
| Phase A | |
| Water | 150.00 g |
| Sodium dodecyl sulphate | 0.375 g |
| Phase B | |
| Fragrance composition 5* | 42.55 g |
| Methacrylic acid | 3.15 g |
| Methyl methacrylate | 1.11 g |
| 1,4-butane diol diacrylate | 2.85 g |
| Lauroyl peroxide | 0.300 g |
| Phase C | |
| Potassium peroxo disulphate @ 2.5% | 0.25 g |
| Water | 9.75 g |

*as described above for example 5

Phase B and then phase A were added to the reactor and the agitator started at time T0. The charge was processed to a finely dispersed emulsion by adjusting the stirring speed to 1100 rpm for 30 minutes at 35° C. while a stream of nitrogen gas was bubbled through the reaction mixture to remove oxygen. The temperature was raised to 70° C. over the course of 15 minutes and allowed to react for a further 4 hours. After 3 hours 1 g of phase C was added to the mixture. After 4 hours the reaction was stopped whereby a microcapsule dispersion was obtained.

The weight ratio of core material to shell material in this example is 5.98:1; those skilled in the art can understand how the ratio can be altered by modifying the quantities of ingredients.

Example 7

Preparation of Microcapsules

A 250 ml closed stirred vessel was fitted with an anchor type stirrer. It was charged in succession with phase A and then Phase B.

| | |
|---|---|
| Phase A | |
| Water | 150.00 g |
| Sodium dodecyl sulphate | 0.375 g |
| Phase B | |
| Fragrance composition 5* | 42.55 g |
| Methacrylic acid | 1.88 g |
| Methyl methacrylate | 0.66 g |
| 1,4-butane diol diacrylate | 1.7 g |
| Lauroyl peroxide | 0.15 g |
| Phase C | |
| Potassium peroxo disulphate @ 2.5% | 0.25 g |
| Water | 9.75 g |

*as described above for example 5

Phase B and then phase A were added to the reactor and the agitator started at time T0. The charge was processed to a finely dispersed emulsion by adjusting the stirring speed to 1100 rpm for 30 minutes at 35° C. while a stream of nitrogen gas was bubbled through the reaction mixture to remove oxygen. The temperature was raised to 70° C. over the course of 15 minutes and allowed to react for a further 4 hours. After 3 hours 1 g of phase C was added to the mixture. After 4 hours the reaction was stopped whereby a microcapsule dispersion was obtained.

The weight ratio of core material to shell material in this example is 10.03:1; those skilled in the art can understand how the ratio can be altered by modifying the quantities of ingredients.

Examples 8-9

Microcapsule Stability in Liquid Detergent

Two microcapsule dispersions were prepared using the procedures of examples 4 and 5. Each dispersion was then dosed at the equivalent of 1.0% of microcapsule dispersion into samples of Henkel Kraft Gel liquid detergent which has a density of 1.070-1.080 g/cm$^3$, and tested for stability. The fragrance composition used in the microcapsules is given in table 8 below:

TABLE 8

| | Fragrance composition | Core to shell weight ratio |
|---|---|---|
| Example 8 | 5 | 1.47:1 |
| Example 9 | 5 | 2.94:1 |

After 1 day storage at 40° C. the microcapsules of both examples 8 and 9 remained well distributed throughout the detergent liquid.

Example 10

Fragrance Composition 6

A fragrance composition for encapsulation was formulated as in table 9 below which shows how the density of the fragrance composition can be varied by adding high density oil soluble organic ingredients (category B ingredients) to fragrance composition 2 to increase the density and to match the density more closely to that of a target liquid consumer product.

TABLE 9

| | wt % Fragrance Composition 2 | wt % Sucrose Octaacetate | Density* (g/cm$^3$) |
|---|---|---|---|
| Fragrance Composition 6 | 70 | 30 | 1.0586 |

*measured at 20° C. according to ASTM D4052

This fragrance composition is suitable for encapsulation by the method of examples 4-7.

Example 11

Fragrance Composition 7

A further example of a fragrance composition of the invention which includes an essential oil is given in table 10 below.

TABLE 10

| Ingredient | CAS No | wt % | Category of material |
|---|---|---|---|
| Amyris oil | 8015-65-4 | 21.44 | A (See table 11) |
| Benzyl acetate | 140-11-4 | 7.16 | A |
| Cedryl methyl ether | 19870-74-7 | 2.30 | A |
| Cedrenyl acetate | 77-54-3 | 2.0 | A |
| Dihydroisojasmonate | 37172-53-5 | 13.24 | A |
| Ethyl vanillin | 121-32-4 | 1.85 | A |
| 2-heptylcyclopentanone | 137-03-1 | 1.43 | C |
| Heliotropine | 120-57-0 | 11.08 | A |
| Undecalactone gamma | 104-67-6 | 1.43 | C |
| (1,7,7-trimethylbicyclo[2,2,1]hept-2-yl)cyclohexanol | 68877-29-2 | 4.07 | C |
| Ethylene brassylate | 105-95-3 | 27.79 | A |
| Triethyl citrate | 77-93-0 | 5.66 | B |
| Isopropyl myristate | 110-27-0 | 0.55 | C |

The major constituents of Amyris oil are listed in table 11 below which accounts for 70.3% by weight of all the constituents of Amyris oil. The oil used had a density of 0.959 g/cm$^3$ as measured at 20° C. according to ASTM D4052 and the major components are cyclic compounds having ClogP values greater than 1.5 but below 6.00. Thus the Amyris oil is a category A ingredient. Seven other high density ingredients with ClogP values between 1.00 and 6.00 and one category B ingredient (triethyl citrate) bring the combined total percentage of high density ingredients to 92.52% by weight of the fragrance composition. This fragrance composition is suitable for encapsulation by the methods of examples 4-7.

TABLE 11

| Ingredient | CAS No | wt % | Mol wt | ClogP |
|---|---|---|---|---|
| Valerianol | 20489-45-6 | 21.5 | 222.4 | 4.62 |
| 7-epi-α-eudesmol | 123123-38-6 | 10.7 | 222.4 | 4.69 |
| Elemol | 639-99-6 | 9.10 | 222.4 | 4.75 |
| β eudesmol | 473-15-4 | 7.9 | 222.4 | 4.68 |
| γ Eudesmol | 1209-71-8 | 6.6 | 222.4 | 4.86 |
| α eudesmol | 473-16-5 | 4.80 | 222.4 | 4.68 |
| β sesqui-phellandrene | 20307-83-9 | 4.70 | 204.3 | 4.70 |
| Selina-3,7(11)diene* | 6813-21-4 | 2.50 | 204.3 | 6.73 |
| Zingiberene* | 495-60-3 | 2.50 | 204.3 | 6.60 |

*zingiberene and Selina-3,7(11)diene have ClogP values outside the 1.00 to 6.00 range.

While the invention has been described in detail and with reference to specific embodiments thereof, it will be apparent to one skilled in the art that various changes and modifications can be made therein without departing from the spirit and scope thereof.

This application is based on European Patent Application No. 10 305 637.0 filed on Jun. 15, 2010, the entire subject matter of which is incorporated herein by reference.

INDUSTRIAL APPLICABILITY

The invention can provide core shell type microcapsules of which fragrance compositions are incorporated into the core to control the delivery and release of fragrance and optionally other benefit agents, when used as components within liquid household, laundry, personal care and cosmetic products.

The invention claimed is:

1. A core shell microcapsule, comprising a core and a shell wherein:
   the shell of the microcapsule is formaldehyde-free and is made of starting materials such that 50%-100% by weight of said materials have a density equal to or less than 1.05 g/cm$^3$; and
   the core of the microcapsule contains a fragrance composition, the fragrance composition comprising:
   a) 20-86.86% by weight of at least one cyclic fragrance material with a density greater than 0.950 g/cm$^3$ and a ClogP in the range from 1.00 to 6.00;
   b) 5.66-50% by weight of at least one oil soluble organic compound having a density greater than 0.950 g/cm$^3$; and
   c) 7.48-80% by weight of at least one material selected from cyclic fragrance ingredients with densities equal to or less than 0.950 g/cm$^3$ and non-cyclic fragrance ingredients with densities which may be greater or less than 0.950 g/cm$^3$;
   where the sum of a), b) and c) equals 100%,
   wherein the weight ratio of core materials to shell materials is in the range from about 50:1 to about 1:1; and
   wherein the component b) is at least one selected from the group consisting of acetyl triethyl citrate, diethyl maleate, diethyl malonate, diethyl adipate, dimethyl adipate, diethyl succinate, diethyl tartarate, glyceryl triacetate, sucrose octa-acetate, sucrose diacetate hexaisobutyrate, glyceryl tripropionate, and triethyl citrate.

2. The core shell microcapsule according to claim 1, wherein at least 60% by weight of the starting materials have a density equal to or less than 1.05 g/cm$^3$.

3. The core shell microcapsule according to claim 1, wherein the said starting materials have a density in the range from 0.700 g/cm$^3$ to 1.05 g/cm$^3$.

4. The core shell microcapsule according to claim 1, wherein the said starting materials comprise at least about 50% by weight of (meth)acrylic acid and/or (meth)acrylates.

5. The core shell microcapsule according to claim 1, wherein the said starting materials comprise from 20% to 75% by weight of one or more cross-linking polymers.

6. The core shell microcapsule according to claim 1, wherein the fragrance composition comprises from 25% to 86.86% by weight of at least one cyclic fragrance material with a density greater than 0.950 g/cm$^3$ and a ClogP in the range from 1.00 to 6.00.

7. The core shell microcapsule according to claim 1, wherein the said at least one cyclic fragrance material has a density in the range from 1.000 g/cm$^3$ to 1.500 g/cm$^3$.

8. The core shell microcapsule according to claim 1, wherein the said at least one cyclic fragrance material has a ClogP in the range from 1.00 to 5.00.

9. The core shell microcapsule according to claim 1, wherein the weight ratio of core materials to shell materials is in the range from about 20:1 to about 1:1.

10. The core shell microcapsule according to claim 1, wherein the core composition has a density in the range from 0.950 g/cm$^3$ to 1.100 g/cm$^3$.

11. A liquid consumer product having a density in the range from 0.900 g/cm$^3$ to 1.400 g/cm$^3$, which comprises the core shell microcapsule as defined in claim 1.

12. The liquid consumer product according to claim 11, which is a household, laundry, personal care or cosmetic composition.

13. The liquid consumer product according to claim 12, which is a fabric softener.

14. The liquid consumer product according to claim 13, which comprises more than 50% by weight water and from about 3% to about 40% by weight of cationic surfactant(s).

15. The core microcapsule according to claim 1, wherein the component c) comprises 2-heptylcyclopentanone, undecalactone gamma, (1,7,7-trimethylbicyclo[2,2,1]hept-2-yl)cyclohexanol and isopropyl myristate.

* * * * *